United States Patent [19]

Roshdy

[11] Patent Number: 5,375,717
[45] Date of Patent: Dec. 27, 1994

[54] FOLDABLE PACKAGE FOR ENDOSCOPIC COMPONENTS AND THE LIKE

[75] Inventor: Constance E. Roshdy, New Egypt, N.J.

[73] Assignee: Ethicon, Inc., Somerville, N.J.

[21] Appl. No.: 114,578

[22] Filed: Aug. 31, 1993

[51] Int. Cl.⁵ .................. A61L 17/02; B65D 85/00; B65D 73/00
[52] U.S. Cl. .................. 206/476; 206/363; 206/364; 206/438; 206/477; 206/482; 206/485; 206/464; 206/571
[58] Field of Search .............. 206/364, 363, 438, 63.3, 206/476, 482, 485, 477, 464, 465, 570, 571

[56] References Cited

U.S. PATENT DOCUMENTS

| | | | |
|---|---|---|---|
| 1,367,600 | 2/1921 | Hirsch | 206/485 |
| 2,024,984 | 12/1935 | Bradley | 206/476 |
| 2,947,415 | 8/1960 | Garth | 206/364 |
| 3,411,620 | 11/1968 | Steinbock | 206/364 |
| 4,023,678 | 5/1977 | Fiedler | 206/363 |
| 4,332,322 | 6/1982 | Jaeschke et al. | 206/364 |
| 4,573,576 | 3/1986 | Krol | 206/438 |
| 4,811,847 | 3/1989 | Reif et al. | 206/571 |
| 4,954,239 | 9/1990 | Mueller | 206/571 |
| 5,076,431 | 12/1991 | Thompson | 206/438 |
| 5,082,112 | 1/1992 | Dunklee | 206/363 |
| 5,131,542 | 7/1992 | Stenström | 206/482 |
| 5,199,561 | 4/1993 | Roshdy et al. | 206/63.3 |
| 5,226,535 | 7/1993 | Rosdhy et al. | 206/364 |
| 5,234,106 | 8/1993 | Transue et al. | 206/363 |

Primary Examiner—Paul T. Sewell
Assistant Examiner—Marie Denise Patterson

[57] ABSTRACT

Packaging for retaining a component together with an instrument package is disclosed. In a preferred embodiment, a foldable package made from a sheet of cut and folded paperboard material is used to retain an endoscope introducer and attach the introducer to an instrument package containing an instrument that is used with the introducer. The disclosed foldable package comprises openings and flaps that retain both the proximal and distal ends of the introducer, and a proximal flap overlies the introducer. The proximal flap is used to release the package and expose the introducer, permitting it to be removed in one smooth motion. Methods of providing prepackaged surgical instruments for a procedure are also disclosed.

12 Claims, 3 Drawing Sheets

FOLDABLE PACKAGE FOR ENDOSCOPIC COMPONENTS AND THE LIKE

The present invention relates to packaging for medical devices and instruments, and more particularly relates to folded paper packages for retaining a component or device together with another package, such as retaining an endoscope introducer with a package containing an endoscopic suture loop and cannula.

BACKGROUND OF THE INVENTION

The packaging of medical devices, and in particular surgical instruments, is subject to a number of competing considerations. First, the packaging must properly surround an protect the device from damage and protect any personnel handling the package from injury. Second, the packaging materials must be chosen to accommodate any sterilization processes required for the device and retain its sterility. This requirement also affects which instruments are packaged together, a consideration also driven by the procedure being performed. It is currently standard practice to try to package instruments and related equipment together into a procedure kit where feasible. Finally, and possibly most importantly, in use the packaging must be unobtrusive and present the packaged items conveniently and quickly. Of course, medical device packages are also subject to more conventional considerations such as the cost of materials, the cost and complexity of tooling to make the package, ease of package assembly, and ease of manufacture and shipping both the empty package and the packaged components. The increasingly competitive economic environment exacerbates these sometimes competing considerations; efficacy must be achieved while costs are maintained at a minimum.

The problems and considerations described above are readily apparent when considering the packaging of devices for endoscopic surgery. The general background of endoscopic surgery is known and is described in co-pending U.S. Patent application Ser. No. 947,662, entitled "Endoscopic Suturing Device," filed on Sep. 18, 1992, now U.S. Pat. No. 5,234,445, which is assigned to the assignee of the present invention and incorporated herein by reference. A package for the type of suture loop and cannula disclosed therein is shown in U.S. Pat. No. 5,226,535. As explained therein, it is desirable to package the suture loop and cannula so that the loop is held in an open position and so that they can be readily removed from the package. It is also explained that these types of instruments are typically placed in a plastic overwrap envelope prior to sterilization, and that the package must therefore protect the overwrap from puncture.

Currently, it is recommended practice that devices such as the suture loop and cannula described in these applications are inserted into the patient using an introducer. In order to ensure that the appropriate size introducer is readily available, it is therefore desirable to package the introducer together with the suture loop cannula. The constraints mentioned above dictate that any package for retaining the introducer must be able to be sterilized together with he suture loop and cannula, and should therefore fit within and not interfere with the plastic overwrap. Moreover, it would be desirable to produce such a package without having to redesign the package for the suture loop and cannula, which is typically sealed within a foil pouch.

Accordingly, it is generally an object of the present invention to provide packaging that will permit components or instruments to be packaged together. It is a further object of the present invention to provide packaging designs that are easily adapted for use with the packaging of existing components. It is another object of the present invention that such packages permit ready and efficient access to the component or instrument that they retain. It is more specifically an object of the present invention to disclose a foldable package for retaining an introducer to a package containing a suture loop and cannula.

SUMMARY OF THE INVENTION

These and other objects are met by providing a foldable package for retaining a component together with an instrument package in accordance with the present invention. Preferably, the foldable package comprises a central panel having longitudinal sides and lateral ends, slits cut inward of the longitudinal sides to create longitudinal retainer flaps, a forward extension portion comprising a proximal tab and an opening for receiving a distal end of the component when folded, and a rearward extension portion comprising an opening for receiving a proximal end of the component when folded. Preferably, the foldable package also has a central retainer that is formed by a central slit surrounding an opening. In a most preferred embodiment, the central retainer comprises a split, raised portion formed by displacing a portion of the central panel, and in certain embodiments a central retainer flap is cut within the split, raised portion.

Certain embodiments of the foldable package of the present invention also include a slit cut inward of a lateral end to create a lateral retainer flap, and may also have a distal retainer flap formed by a slit cut in the rearward extension. In such embodiments, it is preferred that the slit cut in the rearward extension define the opening in the rearward extension. In other preferred embodiments, an opening in the forward extension portion is provided that has one or more locking tabs extending into the opening. In any of these embodiments, one or more predetermined fold lines are preferably formed on the foldable package, most preferably by scoring. The package is preferably comprised of a cardboard material and most preferably is comprised of suture board.

The present invention provides, in a preferred embodiment, a foldable package and an endoscopic component, most preferably an introducer, wherein the foldable package retains the endoscopic component together with an instrument package. The foldable package is most preferably made in the manner described above and includes a central panel having longitudinal sides and lateral ends, slits cut inward of the longitudinal sides to create longitudinal retainer flaps, a forward extension portion comprising a proximal tab and an opening for receiving a distal end of the component when folded, and a rearward extension portion comprising an opening for receiving a proximal end of the component when folded.

Methods of providing prepackaged surgical instruments for a procedure are also disclosed. Preferably, a set of instruments that includes a foldable package attached to an instrument package is provided and a portion of the foldable package is pulled away. Next, a surgical instrument retained by the foldable package, most preferably an endoscope introducer, is removed and the instrument package is then opened.

DETAILED DESCRIPTION OF THE PREFERRED EMBODIMENTS

Figure 1:
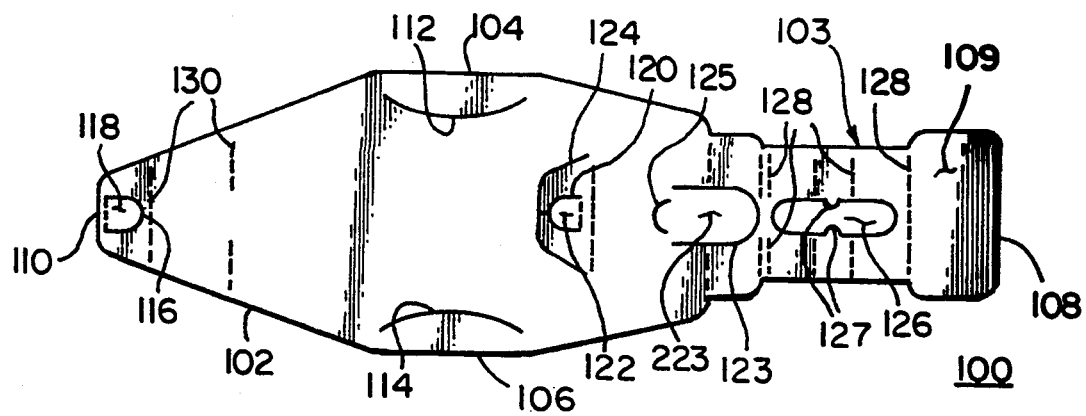
FIG. 1 is a top plan view of a sheet of packaging material cut and scored to create a foldable package in accordance with he present invention.

Referring first to FIG. 1, there is shown a sheet 100 of packaging material cut to create a foldable package in accordance with the present invention. The sheet 100 may be comprised of any foldable material that is acceptable as a package, including fibrous materials, plastics, metals and composites such as laminated sheets or metallized films. In a preferred embodiment, the sheet 100 is comprised of conventional materials such as medical grade paperboard. It is particularly preferred to use a conventional, stiff paperboard having a thickness of about 0.008 to about 0.016 inches familiar to those of ordinary skill. An example of a preferred material is the 0.009 inch thick suture board, such as that sold by Monadnock, Bennington, N.H. The sheet 100 is cut to the configuration shown in FIG. 1 using any of the techniques known in the art and is preferably cut using a steel rule die.

As seen in FIG. 1, the sheet 100 is cut to define a central panel 102 that has longitudinal sides 104,106 and lateral ends 108,110. Retaining slits 112,114 are cut inward of the longitudinal sides to create longitudinal retainer flaps that are displaced to grip the edge of the instrument package (not shown in this view) to which the foldable package is attached. Another slit 125 is cut in the center panel 102 and provides a lateral retainer flap that retains the folded package in place, as explained in further detail below. Inward from the distal end of the sheet 110, a slit 116 is cut to create a distal retainer flap 118. As explained in further detail below, the distal retainer flap 118 is cut so that an opening is formed to permit passage of the component being retained, while being sized so that a frictional fit and the pressure of the distal retainer flap 118 itself effectively retain the component. A somewhat similar function is carried out by a slit 120 that creates a central retainer flap 122 in the central panel 102. Surrounding the opening created by the central retainer flap 122 is another slit 124 that permits the portions surrounding the opening left by the central retainer flap 122 to be raised above the center panel 102 and retain the component, as explained below. Extending from the center panel 102 is a forward extension portion 103 comprising an opening 126 and predetermined fold lines 128. As explained below, when folded, the forward extension portion 103 receives the component being retained, most preferably at its proximal end. Similarly, the distal end 110 of the sheet forms a rearward extension portion comprising an opening formed when the lateral retainer flap 118 is displaced and the sheet is folded along the distal predetermined fold lines 130, so that an end of the component, preferably the distal end, is received when folded.

Figure 2:
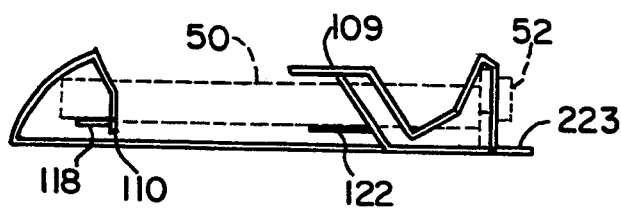
FIG. 2 is a side elevation view of the sheet shown in FIG. 1 that has been folded to accommodate a component.

When the preferred embodiment of the sheet 100 described immediately above is folded along the predetermined fold lines 128,130 a foldable package in accordance with the side view shown in FIG. 2 is constructed. As seen in FIG. 2, the component 50 retained by the foldable package is shown in phantom, and represents an introducer of the type described above that is used to admit an endoscopic suture loop and cannula. As seen in FIG. 2, the distal end 110 of the sheet is folded so that when the distal end of the component 50 is inserted through the opening formed by the slit 116 shown in FIG. 1 it is overlaid by a portion of the sheet 100. As mentioned above, the flap 118 displaced by the component 50 is preferably sized and has sufficient resiliency to press against the component and thus provide a friction fit against this portion of the component 50.

As also shown in FIG. 2, the section of the sheet 100 cut by the slit 124 is displaced upwardly, and the central retainer flap 122 created by the slit 124 is displaced by the component 50 and provides a frictional fit against the component 50, as described immediately above with respect to the flap 118 in the distal end. Referring again to FIG. 1, it should be noted that the displaced section is split so that the component 50 can be snapped into place or removed without longitudinal displacement. Thus, in the preferred embodiment illustrated, the distal end of the component 50 can be inserted into the opening formed when the flap 118 is displaced, and the central portion can be pushed through the split section of the raised central portion formed by the slit 124. It should be noted, however, that it is also possible to insert the distal tip of the component 50 into the opening formed when the central flap 122 is displaced and then slide the component longitudinally until the distal end is retained in the opening formed when the flap 118 is displaced.

The proximal end 108 of the sheet is also folded to retain and protect the component 50. Again referring to FIG. 2, it can be seen that when the proximal end 108 is folded along the predetermined fold lines 128 an opening is formed by the slit 123 through which the proximal end of the component 52 preferably extends, although in certain embodiments, this opening will not be necessary since the component 50 will not extend beyond the proximal end of the package. From this point, the sheet is folded to form a lateral "end wall" and folded back toward the center panel of the package, as shown. The proximal tab 109 described above overlies the raised central portion formed by the slit 124, also described above. This section of the package is retained in place by the locking tabs 127 (seen in FIG. 1) that extend into the opening 126 in the proximal end section 108. The size of the opening 126 is large enough to pass over the component, while the locking tabs 128 extend inwardly an amount sufficient to hold the proximal tab 109 in place by locking against the component 50 after being displaced and pushed over the component 50 into place.

When the sheet illustrated in FIG. 1 is folded into the package shown in FIG. 2, the component 50 will therefore be held securely in place by the various openings, slits and tabs described above. As will be readily apparent to those of ordinary skill, the materials that comprise the foldable package should possess characteristics that permit them to be folded and retain the folded shape and should be strong enough to restrain the component. Thus, the designer of packages in accordance with the present invention should take into account the volume and weight of the component and the orientation in which it is to be presented, among other things, when deciding the size and shape of the various retaining elements. As noted above, in the preferred embodiment illustrated, it has been found that "nine point" suture board provides a foldable package capable of retaining components such as endoscope introducers.

Figure 3:
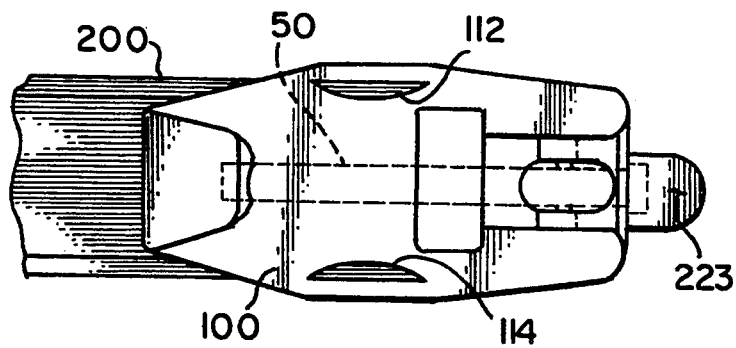
FIG. 3 is a top plan view of the package shown in FIGS. 1-2, also showing the retention of the foldable package on an instrument package.

Another aspect of the present invention is illustrated in FIG. 3. As shown therein, the folded package 100 and component 50 that it holds are preferably attached to an instrument package 200 using the longitudinal flaps formed by the retaining slits 112,114 described above. In a preferred embodiment, the instrument package will comprise a sealed, sterile foil pouch that overlies a relatively rigid package that holds the sterile instrument or component, such as an the suture loop and cannula described above. As seen in FIG. 3, the endpoints of the slits 112,114 are chosen so that when the flap is pushed away, the edges of the opening are sufficiently spaced to permit the instrument package to slide through. Because the flaps most preferably remain connected to the enter pane along the longitudinal edge, the flaps are resiliently hinged and urge against the instrument package 200, most preferably providing a relatively tight frictional fit. It will be appreciated that such a tight sliding fit will stabilize the position of the folded package 100 on the instrument package 200.

Figure 4:
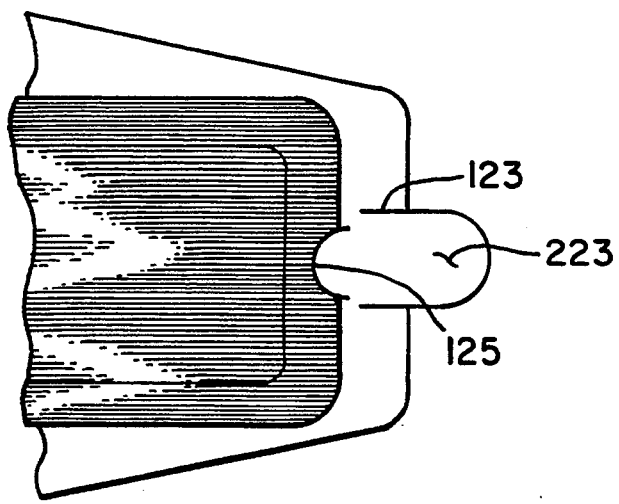
FIG. 4 is an enlarged, partially broken away bottom plan view of the embodiment of the present invention illustrated in FIG. 3.

Despite the tight frictional fit provided along the longitudinal edges, it is sometimes desirable to also ensure retention to one of the lateral edges of the folded package 100 to ensure that it is not displaced along the instrument package 200 during use. As seen in FIG. 4, this function is most preferably accomplished by a lateral retainer flap formed by the slit 125 in the proximal end of the center panel. Also visible in FIG. 3 is the extension 223 formed in certain preferred embodiments by the slit 123 that is also cut in a proximal portion of the central panel 102.

Figure 5:
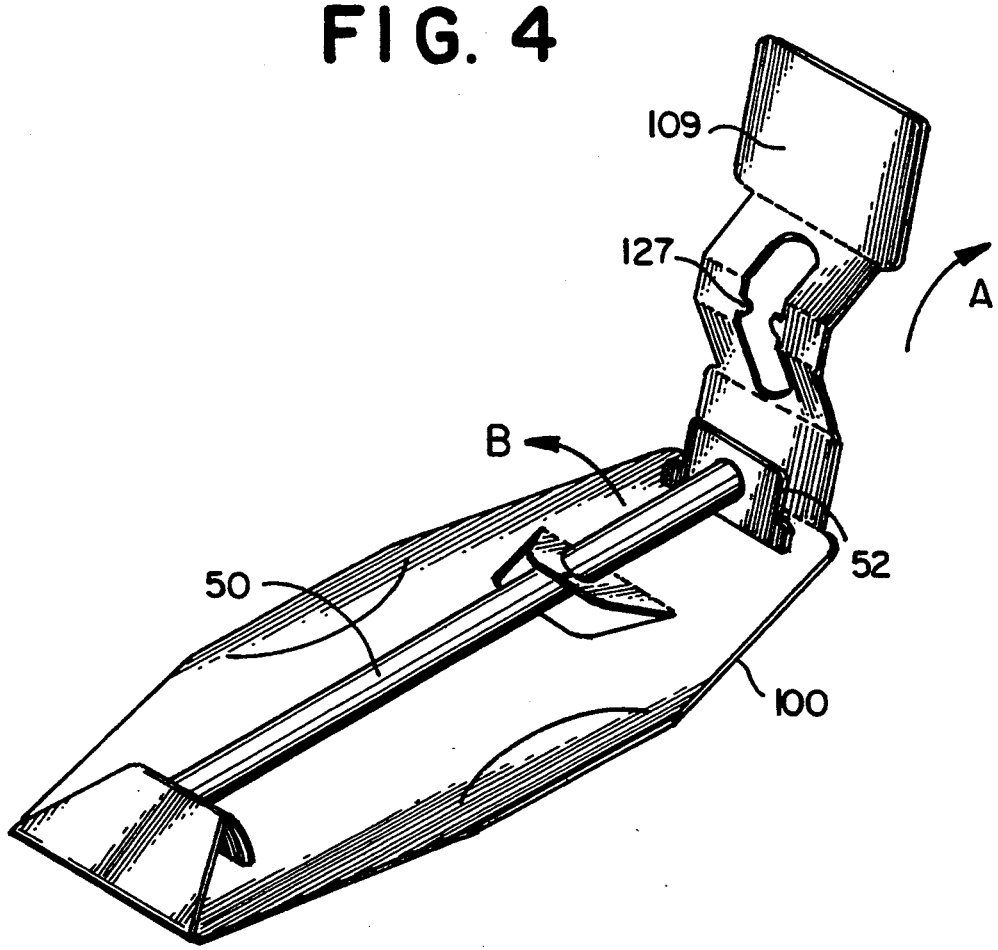
FIG. 5 is a perspective view of the foldable package shown in FIGS. 1-3, illustrating the manner in which the package is opened to provide access to the component.

Referring now to FIG. 5, there is shown a perspective view of the folded package 100 described above and the endoscope introducer 50 that it retains in a most preferred embodiment. The present invention permits access to the introducer 50 while the package 100 is retained on the instrument package 200 (shown in FIGS. 3-4). In use, the combination of the introducer 50 and package 100 are in the position shown in FIG. 3. The proximal tab 109 is grasped and lifted in the direction shown by arrow "A" in FIG. 5. This releases the locking tabs 127, and permits the entire proximal end 52 of the introducer to be exposed as the package 100 is unfolded. At this point, the introducer is still held in position by the raised central portion formed by the slit 124 described above and by the distal retainer flap 118, not visible in this view. The surgeon or nurse next grasps the introducer 50 and pulls it in the direction shown by arrow "B" in FIG. 5. Since the central retainer is preferably split, the introducer 50 is easily disengaged and as it moves though an arc upwardly, the only remaining point of retention is at the distal end. The introducer 50 is then released by simply withdrawing the tip from the opening formed by the slit 116 in the distal end 110 of the package 100. Thus, once the proximal tab 109 is lifted out of the way, as shown in FIG. 5, the introducer is simply grasped and lifted using one hand. It is not necessary to undo or grasp any further retaining portions or the manipulate the introducer 50 in an awkward manner.

Figure 6:
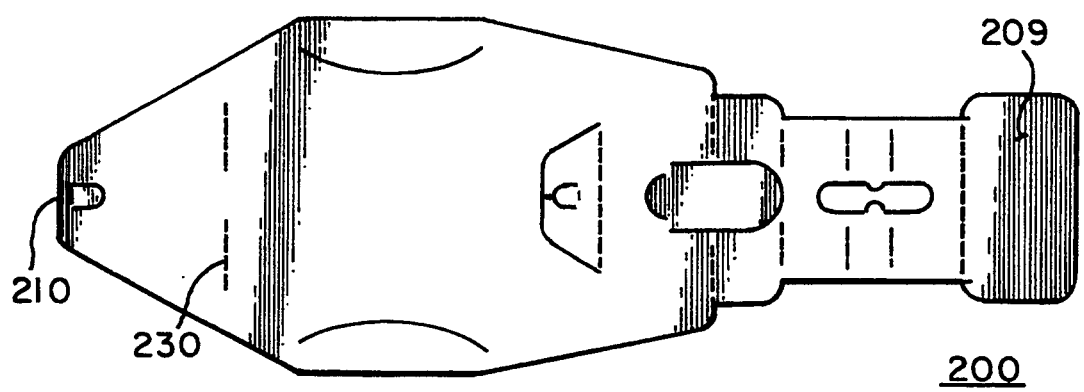
FIG. 6 illustrates another embodiment of the present invention in a view similar to FIG. 1.
Figure 7:
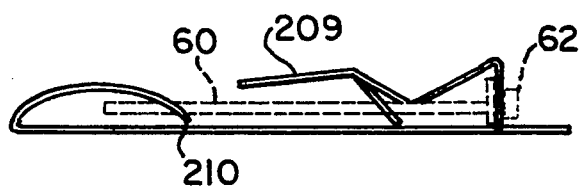
FIG. 7 illustrates a perspective view of the alternate embodiment illustrated in FIG. 6 after the package has been folded and a component inserted.

Another embodiment of the present invention is shown in FIG. 6. Because trocars and related components are provided in a variety of sizes, so too are the introducers used in conjunction with these instruments. The embodiment illustrated with reference to FIGS. 1-5 can be used with most introducers, but is particularly well suited for introducers in the size range of 10 mm. In a preferred embodiment particularly suited for smaller diameter introducers, in the size range of about 5 mm, a sheet 200 is preferably cut in accordance with he pattern shown in FIG. 6. As seen by comparing FIG. 6 to FIG. 1, one difference between the two designs is that only single predetermined fold line 230 is required in the smaller version. Thus, as seen in FIG. 7, this results in the distal end 210 taking on more of an arc shape when folded into a package as shown. FIG. 7 also illustrates the smaller introducer 60 preferably used with this embodiment; a folded proximal section including a distal tab 209 overlies the proximal end 62 and the middle of the introducer 60. The embodiment of FIGS. 6-7 illustrates that the location and relationship of the folds and slits used to create the folded package of the present invention can be varied to suit the geometry of the instrument or component being retained while still accomplishing the functions described above.

Although, as discussed above, the packages of the present invention are preferably constructed from medical grade paperboard, they may be constructed out of any material which is easily die cut and scored, is easily foldable, and which has sufficient strength and integrity to adequately protect the components retained during sterilization, shipping, handling and storage. As noted above, such materials include plastics, foils, and laminates combined with each other or with paper. The packages disclosed herein are preferably made using conventional equipment such as die cutting presses.

It will be appreciated by those skilled in the art that the size of the package will vary in accordance with the size of component that is retained. The package will be of sufficient size to effectively contain a particular component, such as the introducers 50 illustrated and described herein.

The package of the present invention containing a component such as the introducer 50 is typically further packaged by insertion into a conventional overwrap, while the instrument package 200 is typically comprised of a plastic envelope or a conventional foil packet. Such a plastic envelope typically is made from conventional materials such as TYVEK ®, paper polyfoil, polyester copolymer, polypropylene copolymer, combinations thereof, and the like. The packaged medical devices are typically sterilized using conventional sterilization equipment and processes. Examples of the sterilization processes which can be used include conventional sterilization processes such as Cobalt-60 irradiation, ethylene oxide (EtO) sterilization, methylene bromide, and the like.

The one-piece folded package 100 of the present invention has many advantages. It is easy to manufacture using conventional materials and techniques. The package is extremely easy to assemble. The component is retained and protected during sterilization, shipping, and handling. Moreover, as explained above, the package 100 is easily opened in an operating room environment, and the component such as the introducer 50 is easily removed from the package 100 in one continuous motion. The risk of damaging the component during removal from package is therefore substantially eliminated. The package additionally prevents a component such as the introducer 50 illustrated from puncturing or tearing the outer plastic overwrap envelope that typically overlies both the folded package 100 and the instrument package 200.

Although the invention has been shown and described in detail with respect to certain preferred embodiments, it will be understood by those skilled in the art that various changes and further detail thereof may be made without departing from the spirit and scope of the claimed invention. Accordingly, reference should be made to the appended claims in order to determine the full scope of the present invention.

What is claimed is:

1. A packaging system for an endoscopic instrument and an endoscopic introducer for said instrument comprising: an instrument package having opposed sides and opposed ends adapted to contain an endoscopic instrument, a foldable package for retaining said introducer removably affixed said instrument package, said foldable package comprising: a central panel having longitudinal sides and lateral ends; slits cut inward of the longitudinal sides to create longitudinal retainer flaps adapted to engage the sides of said instrument package; a forward extension portion comprising a proximal tab and an opening for receiving a distal end of the introducer when folded; and a rearward extension portion comprising an opening for receiving a proximal end of the introducer when folded.

2. The packaging system of claim 1 in which the foldable package further comprises a central retainer comprising a split, raised portion formed by displacing a portion of the central panel.

3. The packaging system of claim 2 in which the foldable package further comprises a central retainer flap cut within the split, raised portion.

4. The packaging system of claim 1 in which the foldable package further comprises a slit cut inward of a lateral end to create a lateral retainer flap.

5. The packaging system of claim 1 in which the foldable package further comprises a distal retainer flap formed by a slit cut in the rearward extension.

6. The packaging system of claim 5 wherein the slit cut in the rearward extension defines the opening in the rearward extension.

7. The packaging system of claim 1 wherein the forward extension portion further comprises an opening and at least one locking tab extending into the opening.

8. The packaging system of claim 1 in which the foldable package further comprises at least one predetermined fold lines.

9. The packaging system of claim 8, wherein the predetermined fold lines are formed by scoring.

10. The packaging system of claim 1 wherein the foldable package is comprised of a paperboard material.

11. The packaging system of claim 10, wherein the foldable package is comprised of suture board material having a thickness between about 0.008 and 0.016 inches.

12. The packaging system of claim 1 further comprising an overwrap containing both the instrument package and the foldable package.

* * * * *